US00PP15241P2

(12) United States Plant Patent
Arimitsu

(10) Patent No.: US PP15,241 P2
(45) Date of Patent: Oct. 19, 2004

(54) *VERBENA* PLANT NAMED 'BODCOMPUR'

(50) Latin Name: *Verbena hybrida*
Varietal Denomination: Bodcompur

(75) Inventor: Yoshiro Arimitsu, Lompoc, CA (US)

(73) Assignee: John Bodger + Sons Co., South El Monte, CA (US)

( * ) Notice: Subject to any disclaimer, the term of this patent is extended or adjusted under 35 U.S.C. 154(b) by 0 days.

(21) Appl. No.: 10/684,562

(22) Filed: Oct. 13, 2003

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Bodcompur', characterized by its compact, upright and mounded plant habit; freely branching habit; dense and bushy growth habit; dark green-colored leaves; and dark purple-colored flowers with flowers held above and beyond the foliage.

1 Drawing Sheet

Botanical classification/cultivar designation: *Verbena hybrida* cultivar Bodcompur.

BACKGROUND OF THE INVENTION

The present Invention relates to a new and distinct cultivar of *Verbena* plant, botanically known as *Verbena hybrida,* and hereinafter referred to by the name 'Bodcompur'.

The new *Verbena* is a product of a planned breeding program conducted by the Inventor in Lompoc, Calif. The objective of the breeding program is to develop new *Verbena* cultivars with a dense and bushy growth habit, numerous flowers, and interesting flower and foliage colors.

The new *Verbena* originated from a cross-pollination made by the Inventor in July, 1991 of the *Verbena hybrida* cultivar Amore Purple, not patented, as the female, or seed, parent with a proprietary *Verbena hybrida* selection identified as 1V238, not patented, as the male, or pollen, parent. The cultivar Bodcompur was discovered and selected by the Inventor as a flowering plant within the progeny from this cross-pollination in a controlled environment in Lompoc, Calif.

Asexual reproduction of the new cultivar by terminal cuttings in a controlled environment in Lompoc, Calif. has shown that the unique feature of this new *Verbena* are stable and reproduced true to type in successive generations of asexual reproduction.

SUMMARY OF THE INVENTION

The following traits have been repeatedly observed and are determined to be the unique characteristics of 'Bodcompur'. These characteristics in combination distinguish 'Bodcompur' as a new and distinct cultivar:

1. Compact, upright and mounded plant habit.
2. Freely branching habit; dense and bushy growth habit.
3. Dark green-colored leaves.
4. Dark purple-colored flowers with flowers held above and beyond the foliage.

Plants of the new *Verbena* differ primarily from plants of the parents in plant habit and flower coloration.

Plants of the new *Verbena* differ primarily from plants of the cultivar Bodcompureye, disclosed in a U.S. Plant patent application Ser. No. 10/684,533, in flower coloration.

Plants of the new *Verbena* can be compared to plants of the cultivar Obsession Purple, not patented. In side-by-side comparisons conducted in Lompoc, Calif., plants of the new *Verbena* differed primarily from plants of the cultivar Obsession Purple in plant and flower form as plants of the cultivar Obsession Purple are more mounded and have narrower petals than plants of the new *Verbena*.

Plants of the new *Verbena* can also be compared to plants of the cultivar Sandy Rose, not patented. In side-by-side comparisons conducted in Lompoc, Calif., plants of the new *Verbena* differed primarily from plants of the cultivar Sandy Rose in plant form as plants of the cultivar Sandy Rose are more upright and taller than plants of the new *Verbena*.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description which accurately describe the colors of the new *Verbena*.

The photograph at the top of the sheet comprises a side perspective view of a typical flowering plant of 'Bodcompur' grown in a container.

The photograph at the bottom of the sheet comprises a close-up view of typical inflorescences, flowers and leaves of 'Bodcompur'.

DETAILED BOTANICAL DESCRIPTION

The cultivar Bodcompur has not been observed under all possible environmental conditions. The phenotype may vary somewhat with variations in environment such as temperature and light intensity without, however, any variance in genotype. The aforementioned photographs and following observations and measurements describe plants grown in Lompoc, Calif., under commercial practice during the summer in a polycarbonate-covered greenhouse with day temperatures about 21 to 27° C., night temperatures about 16 to 18° C., and light levels about 4,000 to 8,000 foot-candles. Cuttings were planted in 10-cm containers, pinched one time, and grown for about seven weeks. In the following description, color references are made to The Royal Horticultural Society Colour Chart, 1995 Edition, except where general terms of ordinary dictionary significance are used.

Botanical classification: *Verbena hybrida* cultivar Bodcompur.

Parentage:

*Female, or seed, parent.*—*Verbena hybrida* cultivar Amore Purple, not patented.

*Male, or pollen, parent.*—Proprietary *Verbena hybrida* selection identified as 1V238, not patented.

Propagation:

*Type cutting.*—Terminal cuttings.

*Time to initiate roots, summer.*—About 7 to 10 days at 26° C.

*Time to initiate roots, winter.*—About 21 days at 26° C.

*Time to produce a rooted cutting or liner, summer.*—About 21 days at 26° C.

*Time to produce a rooted cutting or liner, winter.*—About 28 days at 26° C.

*Root description.*—Fine, fibrous, white in color.

*Rooting habit.*—Freely branching; dense.

Plant description:

*Form.*—Compact, upright and mounded plant habit.

*Growth and branching habit.*—Moderately vigorous and freely-branching with about 16 to 18 lateral branches developing after the pinch, dense and bushy growth habit.

*Plant height.*—About 16 cm.

*Plant diameter or spread.*—About 24 cm.

*Lateral branches.*—Length: About 14 cm. Diameter: About 2.5 mm. Internode length: About 2.25 cm. Texture: Pubescent. Color: 145B.

*Foliage description.*—Arrangement: Opposite, simple. Length: About 4.5 cm. Width: About 2.8 cm. Shape: Deltoid. Apex: Broadly acute. Base: Acute to attenuate. Margin: Irregularly crenate. Texture, upper and lower surfaces: Coarse, pubescent. Venation pattern: Pinnate. Color: Developing foliage, upper surface: 137B. Developing foliage, lower surface: 147B. Fully expanded, upper surface: 147A. Fully expanded, lower surface: 147B. Venation, upper surface: 143C. Venation, lower surface: 143D. Petiole: Length: About 2 cm. Diameter: About 2 mm. Color: 143B.

Flower description:

*Flower type and habit.*—Single upright salverform flowers arranged on compact terminal racemes; flowers sessile. Freely flowering with about 22 flowers and flower buds per raceme; about two to three racemes per lateral branch. Inflorescences positioned above and beyond the foliage. Flowers last about four days under greenhouse conditions. Flowers not persistent.

*Fragrance.*—None detected.

*Flowering season.*—In the garden, flowering is continuous from spring until fall.

*Inflorescence height.*—About 2.75 cm.

*Inflorescence diameter.*—About 6 cm.

*Flower size.*—Diameter: About 2 cm. Tube length: About 2.2 cm. Throat diameter: About 2 mm. Tube diameter, at base: About 2 mm.

*Flower buds.*—Rate of opening, from showing color to fully open flower: About two days. Length: About 1.4 cm. Diameter, apex: About 3.5 mm. Diameter, base: About 2.5 mm. Shape: Tubular, oblong. Color: 86B.

*Petals.*—Quantity/arrangement: Five per flower fused at base. Lobe length: About 1 cm. Lobe width: About 1 cm. Shape: Roughly cordate. Apex: Emarginate. Margin: Entire. Texture, upper and lower surfaces: Velvety, smooth. Color: When opening, upper surface: Brighter than 79B. When opening, lower surface: 83C to 83D. Fully opened, upper surface: Brighter than 77A; color becoming closer to 77A to 77B with development. Fully opened, lower surface: 83A to 83B. Throat: 155C. Tube: 155D.

*Sepals.*—Quantity/arrangement: Five, fused into a tube. Length: About 1.2 cm. Diameter: About 3 mm. Shape: Ligulate. Apex: Acute. Margin: Entire. Texture, upper and lower surfaces: Coarse, pubescent. Color, upper surface: 143D. Color, lower surface: 143B.

*Peduncles.*—Length: About 5.3 cm. Diameter: About 1.5 mm. Angle: Upright to about 45° from vertical. Strength: Strong. Color: 144A.

*Reproductive organs.*—Stamens: Quantity per flower: Four; adnate to pistil. Anther shape: Oval. Anther length: Less than 1 mm. Anther color: 145A. Pollen amount: Scarce. Pollen color: 145A. Pistils: Quantity per flower: One. Pistil length: About 1.8 cm. Stigma shape: Bi-parted. Stigma color: 144B. Style length: About 1.6 cm. Style color: 144D. Ovary color: 144C to 144D.

*Fruit/seed.*—Fruit and seed production has not been observed.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranging from 2 to 40° C.

It is claimed:

1. A new and distinct cultivar of *Verbena* plant named 'Bodcompur', as illustrated and described.

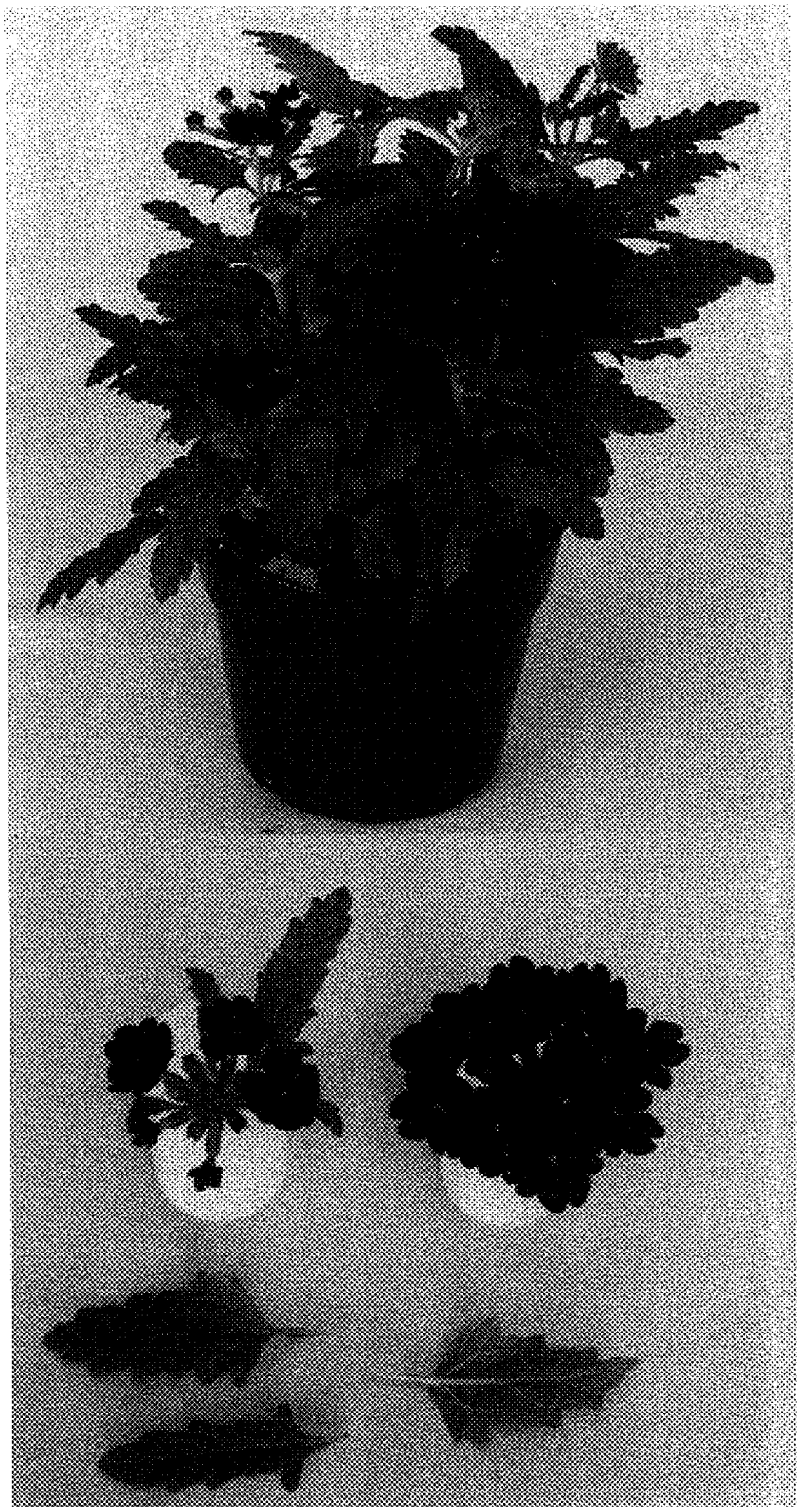

* * * * *